US00PP14490P29

(12) United States Plant Patent
Westhoff

(10) Patent No.: US PP14,490 P2
(45) Date of Patent: Jan. 27, 2004

(54) PETUNIA PLANT NAMED 'WESPEVAN'

(50) Latin Name: *Petunia×hybrida*
Varietal Denomination: Wespevan

(75) Inventor: Heinrich Westhoff, Südlohn (DE)

(73) Assignee: Josef & Heinrich Westhoff Gartenbau-Spezialkulturen, Südlohln-Oeding (DE)

( * ) Notice: Subject to any disclaimer, the term of this patent is extended or adjusted under 35 U.S.C. 154(b) by 0 days.

(21) Appl. No.: 10/317,308

(22) Filed: Dec. 12, 2002

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Petunia plant named 'Wespevan', characterized by its upright and outwardly spreading plant habit; freely branching habit; short internodes, dense and bushy growth habit; freely flowering habit; and single salverform light yellow-colored flowers with light green to yellow-colored venation.

1 Drawing Sheet

Botanical classification/cultivar designation: Petunax×hybrida cultivar Wespevan.

BACKGROUND OF THE INVENTION

The present Invention relates to a new and distinct cultivar of Petunia plant, botanically known as Petunia×hybrida, and hereinafter referred to by the name 'Wespevan'.

The new Petunia is a product of a planned breeding program conducted by the Inventor in Sudlohn-Oeding, Germany. The new Petunia originated from a cross-pollination made by the Inventor of a proprietary Petunia selection identified as 99 P 87, not patented, as the female, or seed, parent with a proprietary Petunia selection identified as 99 P 93, not patented, as the male, or pollen, parent. The new Petunia was selected by the Inventor in 2000 in a controlled environment in Sudlohn-Oeding, Germany.

Asexual reproduction of the new cultivar by terminal cuttings taken in Sudlohn-Oeding, Germany since 2001, has shown that the unique features of this new Petunia are stable and reproduced true to type in successive generations.

SUMMARY OF THE INVENTION

Plants of the cultivar Wespevan have not been observed under all possible environmental conditions. The phenotype may vary somewhat with variations in environment such as temperature and light intensity without, however, any variance in genotype.

The following traits have been repeatedly observed and are determined to be the unique characteristics of 'Wespevan'. These characteristics in combination distinguish 'Wespevan' as a new and distinct Petunia cultivar:

1. Upright and outwardly spreading plant habit.
2. Freely branching habit.
3. Short internodes, dense and bushy growth habit.
4. Freely flowering habit.
5. Single salverform light yellow-colored flowers with light green to yellow-colored venation.

Plants of the new Petunia are more outwardly spreading, have smaller flowers and darker yellow-colored flowers than plants of the female parent, the selection 99 P 87. Plants of the new Petunia have darker green-colored leaves and darker yellow-colored flowers than plants of the male parent, the selection 99 P 93.

Plants of the cultivar Wespevan can be compared to plants of the Petunia cultivar Lemon Plum, not patented. However in side-by-side comparisons conducted in Sudlohn-Oeding, Germany, plants of the new Petunia and the cultivar Lemon Plum differed in the following characteristics:

1. Plants of the new Petunia were more upright than plants of the cultivar Lemon Plum.
2. Plants of the new Petunia were more compact and had shorter internodes than plants of the cultivar Lemon Plum.
3. Plants of the new Petunia had smaller and darker green-colored leaves than plants of the cultivar Lemon Plum.
4. Plants of the new Petunia had smaller flowers than plants of the cultivar Lemon Plum.
5. Plants of the new Petunia had smaller sepals than plants of the cultivar Lemon Plum.

Plants of the cultivar Wespevan can also be compared to plants of the Petunia cultivar Lime, not patented. However in side-by-side comparisons conducted in Sudlohn-Oeding, Germany, plants of the new Petunia and the cultivar Lime differed in the following characteristics:

1. Plants of the new Petunia were more upright than plants of the cultivar Lime.
2. Plants of the new Petunia were more compact and had shorter internodes than plants of the cultivar Lime.
3. Plants of the new Petunia had smaller leaves than plants of the cultivar Lime.
4. Plants of the new Petunia had smaller flowers than plants of the cultivar Lime.
5. Plants of the new Petunia had smaller sepals than plants of the cultivar Lime.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical plant of 'Wespevan'.

The photograph at the bottom of the sheet comprises a close-up view of a typical flower and leaves of 'Wespevan'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and the description were grown in 12-cm containers during the spring and summer for about 20 weeks in a glass-covered greenhouse and under conditions which closely approximate commercial production conditions in Sudlohn-Oeding, Germany. During the production of the plants, day temperatures were about 20 to 25° C., night temperatures were about 16 to 18° C. and light levels ranged from 3,000 to 50,000 lux.

Botanical classification: Petunia×hybrida cultivar Wespevan.

Parentage:

*Female parent.*—Proprietary Petunia×hybrida selection identified as 99 P 87, not patented.

*Male parent.*—Proprietary Petunia×hybrida selection identified as 99 P 93, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Numerous, fine, fibrous and well-branched.

Plant description:

*Form.*—Annual flowering plant; upright and outwardly spreading. Viscid, glandular pubescent. Freely continuous basal branching with lateral branches potentially forming at every node.

*Usage.*—Appropriate for hanging baskets, window boxes and patio containers.

*Plant height (from soil level to top of plant plane).*—About 27 cm.

*Plant diameter.*—About 35 to 45 cm.

*Stem description.*—Main branches, length: About 38 cm. Main branches, diameter: About 4.5 mm. Lateral branches, length: About 18.5 cm. Lateral branches, diameter: About 2.25 mm. Internode length: About 2.6 cm. Texture: Densely pubescence. Color: 146A.

*Foliage description.*—Arrangement: Alternate; simple. Length: About 4.4 cm. Width: About 2.25 cm. Shape: Ovate. Apex: Acute. Base: Attenuate. Margin: Entire. Aspect: Flat. Texture, upper and lower surfaces: Pubescent. Venation pattern: Pinnate. Color: Young foliage, upper surface: 147A. Young foliage, lower surface: 147B. Mature foliage, upper surface: 147A to 147B. Mature foliage, lower surface: 147B. Venation, upper surface: 146B. Venation, lower surface: 146C. Petiole length: About 1 cm. Petiole diameter: About 2.5 mm. Petiole color: 147C.

Flower description:

*Flower type and habit.*—Single salverform flowers; flowers face upward and outward; single, axillary. Flowers persistent. Freely flowering.

*Natural flowering season.*—Long day responsive; flowering from April until frost in the autumn in Germany; flowering continuous during this period.

*Fragrance.*—None detected.

*Flower longevity on the plant.*—About one week.

*Flower size.*—Diameter: About 5.5 cm. Depth (height): About 3.2 cm. Tube length: About 2.6 cm. Throat diameter, distal end: About 1.25 cm. Tube diameter, proximal end: About 4 mm.

*Flower buds.*—Length: About 2.5 cm. Diameter: About 5.7 mm. Shape: Oblong. Color, towards apex: 150C. Color, midsection and base: 144C.

*Petals.*—Arrangement/appearance: Single whorls of five petals, fused into flared trumpet. Length from throat: About 2.6 cm. Width: About 3 cm. Shape: Roughly spatulate. Apex: Obtuse. Margin: Entire, slightly undulate. Texture, upper and lower surfaces: Smooth, satiny. Color: When opening, upper surface: 155A to 1C. When opening, lower surface: 1C. Fully opened, upper surface: 4C to 6B; color becoming closer to 2C with development. Fully opened, lower surface: 4C to 6B. Flower throat (inside): 4B to 12A. Flower tube (outside): 6C. Venation, upper surface: Primary vein, 144B; secondary veins, 12A. Venation, lower surface: Primary vein, 144B; secondary veins, 154B. Venation, throat: Primary vein, 144B; secondary veins, 12A. Venation, tube: 144B.

*Sepals.*—Arrangement/appearance: Single whorl of five sepals, fused at base; star-shaped. Length: About 1.5 cm. Width: About 2.6 mm. Shape: Linear. Apex: Obtuse. Margin: Entire. Texture, upper and lower surfaces: Densely pubescent; leathery. Color, upper surface: 146A. Color, lower surface: 146B.

*Peduncles.*—Length: About 2.4 cm. Width: About 1.1 mm. Strength: Flexible and wiry. Texture: Pubescent. Color: 144A to 144B.

*Reproductive organs.*—Stamens: Quantity: About five per flower. Anther shape: Four-parted, reniform. Anther length: About 3 mm. Anther width: About 2 mm. Anther color: 8B. Pollen amount: Abundant. Pollen color: 8C. Pistils: Quantity: One per flower. Pistil length: About 2.7 cm. Stigma shape: Rounded to squarish. Stigma color, immature: 144A. Stigma color, mature: 144A to 144B. Style length: About 1.9 cm. Style color: 145A. Ovary color: 144A. Seed/fruit: Seed and fruit production have not been observed.

Disease/pest resistance: Plants of the new Petunia have not been noted to be resistant to pathogens or pests common to Petunia.

Temperature tolerance: Plants of the new Petunia have been observed to be tolerant to temperatures from 4 to 30° C.

It is claimed:

1. A new and distinct cultivar of Petunia plant named 'Wespevan', as illustrated and described.

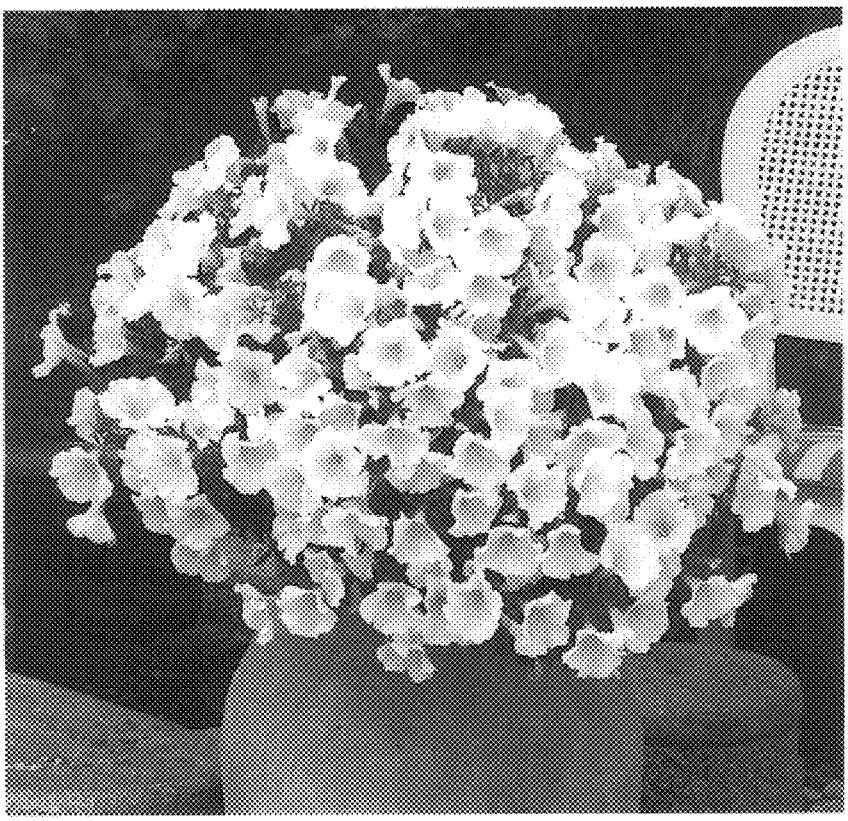
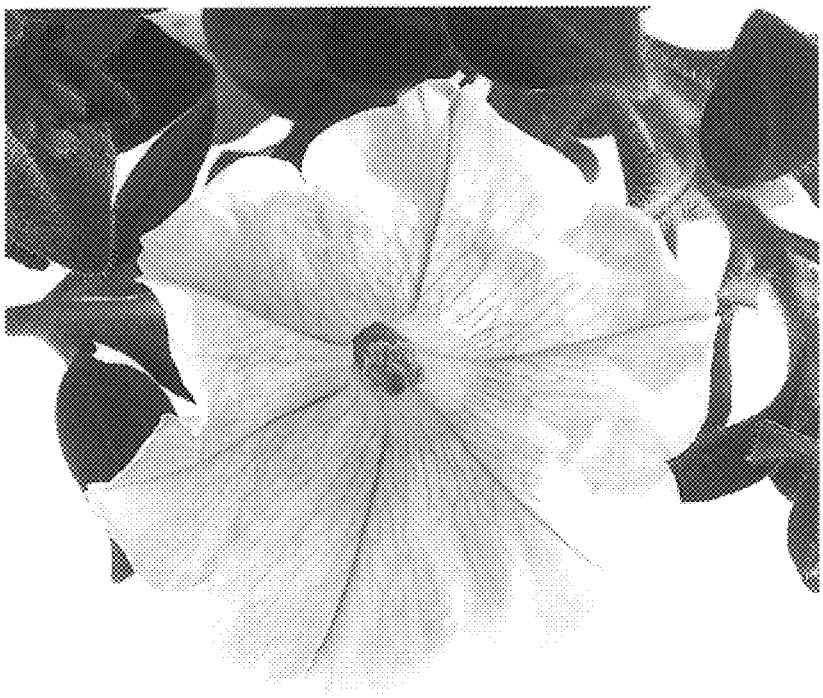

* * * * *